United States Patent [19]

Eturi et al.

[11] Patent Number: 5,969,155
[45] Date of Patent: Oct. 19, 1999

[54] CONVERSION OF TRINITROTOLUENE INTO HIGH VALUE COMPOUNDS

[75] Inventors: Sreenivasa R. Eturi, Budd Lake; Abdollah Bashir-Hashemi, Bridgewater; Sury Iyer, Randolph, all of N.J.

[73] Assignee: The United States of America as represented by the Secretary of the Army, Washington, D.C.

[21] Appl. No.: 09/057,950

[22] Filed: Apr. 9, 1998

Related U.S. Application Data

[60] Provisional application No. 60/043,849, Apr. 11, 1997.

[51] Int. Cl.⁶ .................................................. C07D 209/08
[52] U.S. Cl. ........................................ 548/509; 548/508
[58] Field of Search ............................................. 548/509

[56] References Cited

U.S. PATENT DOCUMENTS 5,210,214  5/1993  Diehl et al. ............................... 548/439

OTHER PUBLICATIONS

Roue et al., Efficient monotitration of indolic compounds . . . , Heterocycles 43(2), 263–6 (see STN abstract), Dec. 1996.

*Primary Examiner*—Robert W. Ramsuer
*Assistant Examiner*—Dominic Keating
*Attorney, Agent, or Firm*—John Moran; John Callaghan

[57] ABSTRACT

The present invention is directed to the synthesis of useful products from the explosive trinitrotoluene. This substance has a limited shelf life as a reliable explosive and large quantities of it have and will become surplus. Ecologically safe, and preferably commercially useful ways of disposing of it are therefore much to be desired. In the present invention the end products are nitroindoles of the general formula 4-$Z^1$,6-$Z^2$ indole wherein $Z^1$ and $Z^2$ are the same or different and are halo or nitro provided at least one of said groups is nitro.

5 Claims, 1 Drawing Sheet

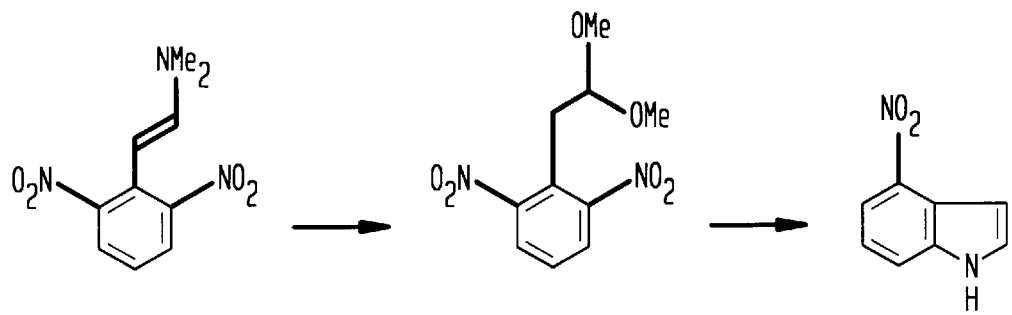
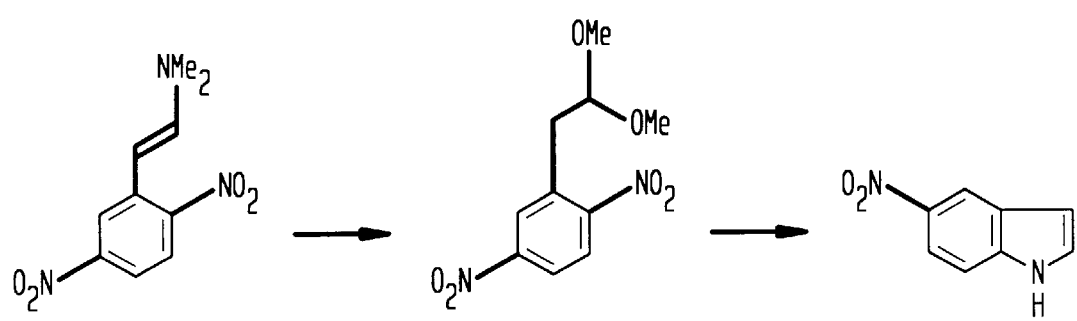
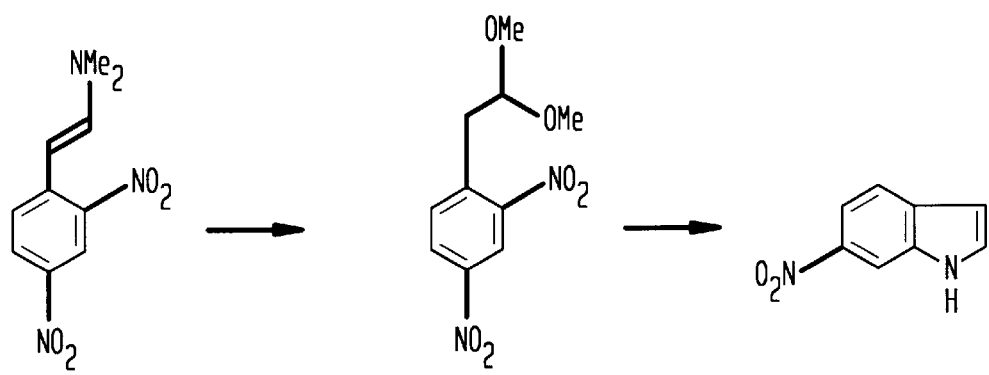

CONVERSION OF TRINITROTOLUENE INTO HIGH VALUE COMPOUNDS

RELATED APPLICATIONS

This application claims priority of Provisional application Ser. No. 60/043849, filed Apr. 11, 1997.

GOVERNMENTAL INTEREST

The Government has rights in this invention pursuant to Contract No. DAAA21-89-C-0013 awarded by the U.S. Army.

The invention described herein was made under a contract with the Government and may be used and licensed by or for the government for Governmental purposes without payment to us of any royalties.

FIELD OF USE

This invention describes an efficient synthesis of high value materials from energetic compounds.

BACKGROUND OF THE INVENTION

Scaling down of munitions manufacture and a need to dispose large quantities of stockpiled explosives initiated for a program conversion of such high energetic material such as TNT into high value civilian products. Such an application is cost-efficient to dispose of unwanted high energetic materials.

The products of the present invention can find diverse synthetic applications in developing novel compounds as nonlinear optical material and substituted derivatives useful as agrochemicals and pharmaceutical compounds.

Discovery of organic Nonlinear Optical Materials has received considerable attention from academic and industrial researchers as they are recognized as the materials of the future. (Introduction to Nonlinear Optical Effects in Molecules & Polymers; P. N. Prasad and D. J. Williams; John Wiley & Sons, Inc., New York, N.Y. 1991). Nonlinear optical materials have potential use in future technology of photonics which would utilize optical frequency conversion, optical signal processing and image processing using ultrashort laser pulses. Organic molecules with electron donor and acceptor groups connected by a p-electron structure offer several advantages in flexibility of molecular structures and conformations and ability to various device structures such as films and fibers.

Indole derivatives are useful as intermediate compounds to prepare agricultural or pharmaceutical substances. However, certain indole derivatives are difficult to prepare via conventional synthetic routes, particularly 4,6-disubstituted indoles. Trinitrotoluene, with its prior structural architecture, provides an easy access to prepare several disubstituted indoles in which at least one is a nitro group.

SUMMARY OF THE INVENTION

The present invention is directed to the synthesis of useful products from the explosive trinitrotoluene. This substance has a limited shelf life as a reliable explosive and large quantities of it have and will become surplus. Ecologically safe, and preferably commercially useful ways of disposing of it are therefore much to be desired. In the present invention the end products are nitroindoles of the general formula 4-$Z^1$,6-$Z^2$ indole wherein $Z^1$ and $Z^2$ are the same or different and are halo or nitro provided at least one of said groups is nitro.

The halo group may be fluoro, chloro or bromo, suitably chloro. Q may be lower alkyl of $C_1$ to $C_6$, preferably methyl or ethyl.

The process of preparing the nitroindoles of the present invention comprises the sequential steps of reacting a 2-$R^1$, 4-$R^2$,6-$R^3$ toluene wherein $R^1$,$R^2$ and $R^3$ are the same or different and are Q.O-, halo or nitro provided at least two of said groups are nitro with an N,N-dimethylformamide di(Q)-acetal to yield β-N,N-di(Q)-2-$R^1$,4-$R^2$,6-$R^3$ styrene, and treating said product with a strong acid, suitably in catalytic amounts, such as a strong organic acid or, preferably, concentrated hydrochloric acid to yield the corresponding 1-[2,2-di(Q.O)]ethyl-2-$R^1$,4-$R^2$,6-$R^3$ benzene and reacting this product with a metal, suitably iron, preferably iron powder or iron filings, in an acid, suitably an organic acid such as acetic acid or the like to yield the appropriate nitroindole.

The intermediates in this sequence have utility as polymer precursors. The β-N,N-di(Q)-2-$R^1$,4-$R^2$,6-$R^3$ styrenes are useful in the formation of NLOs (Non Linear Optical) materials.

4,6-Dinitroindole may be prepared by reacting a 2-Amino-4,6-dinitrotoluene (readily obtainable by reduction of trinitrotoluene) with an N,N-dimethylformamide di(Q) acetal suitably wherein Q is methyl to yield β-N,N-dimethyl-2-amino-4,6-dinitrostyrene which, by reaction with a strong organic to yield the 4,6 dinitroindole directly.

Other aspects of this invention include the conversion of 2-amino-4,6 dinitrotoluene (J. Org. Chem, 51, 2572, 1986) to the 2,6-diamino-4-nitrotoluene with iron in the presence of acetic acid and the conversion of TNT into 2,6-dinitro-4-aminotoluene with Bakers yeast. Both of these compounds are useful in the synthesis of conductive polyazo and polyazomethines.

2,6-diamino-4-nitrotoluene by reaction with sodium nitrite in the presence of cuprous chloride and hydrochloric acid yields 2,6-chloro-4-nitrotoluene which is brominated with N-Bromosuccinimide and AIBN in carbon tetrachloride to yield 1-bromomethyl-2,6-dichloro-4-nitrobenzene, this in turn on treatment with $NaCMe_2NO_2$ in dimethyl sulfoxide yields 2,6-dichloro-4-nitrobenzaldehyde. This may be polymerized to a 2,6-dichloro-1,4-phenylpolyimine.

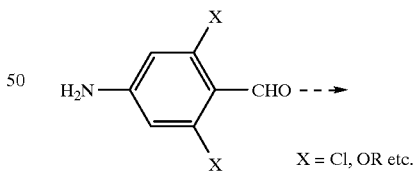

X = Cl, OR etc.

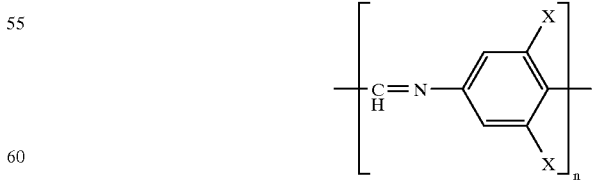

7

Other conductive polyimines may be prepared by refluxing 2,6-diamino-4-nitrotoluene in acetic acid with 2,5-R-benzene-1,4-dialdehyde, where R is hydrogen or methyl.

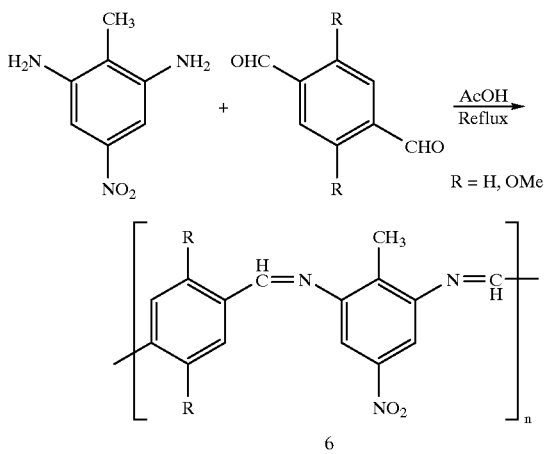

In addition to the NLO materials β-N,N-Dimethylamino-2,4,6-trinitrostyrene and β-N,N-Dimethylamino-2-amino-4,6-dinitrostyrene mentioned hereinbelow, reaction of TNT with 4-dimethylaminobenzaldehyde in place of dimethylformamide dimethylacetal yields β-[4-(N,N-Diethylamino) phenyl]-2,4,6-trinitrostyrene.

BRIEF DESCRIPTION OF THE DRAWINGS

The FIGURE is a flow diagram of the reactions and compounds of the present invention.

DESCRIPTION OF THE PREFERRED EMBODIMENTS

The conversion of trinitrotoluene to various dinitrotoluenes variously substituted by an amino, a halo or an alkoxy group are well known in the art. All these are to be considered as starting materials for the disposal of trinitrotoluene.

The starting materials namely 2-$R^1$,4-$R^2$,6-$R^3$ toluene wherein $R^1$,$R^2$ and $R^3$ are the same or different and are halo or nitro provided at least two of said groups are nitro are heated, suitably under reflux, preferably with an excess, most preferably a 10–30% molar excess of N,N-dimethylformamide dimethylacetal in an inert atmosphere, suitably a nitrogen atmosphere. A precipitate is formed which is separated by filtration and washed with ether to yield the corresponding β-N,N-dimethyl-2-$R^1$,4-$R^2$,6-$R^3$ styrene. In place of the dimethyl acetal other dialkyl or diaralkyl acetals, such as di-ethyl, propyl, butyl, benzyl acetals may be used to give the corresponding N,N-di substituted products.

The β-N,N-dimethyl-2-$R^1$,4-$R^2$,6-$R^3$ styrene (or corresponding dialkyl or diaralkyl analogs) is taken up in an alkanol, suitably methanol and heated, suitably under reflux with a catalytic amount, suitably about 0.01 to about 0.1 equivalents of a strong acid such as hydrochloric or p-toluene sulfonic acids, for from about 1 to about 4 hours, preferably for about 2–2.5 hours. The solvent is then removed under reduced pressure, the residue diluted with water and extracted with a suitable water immiscible polar organic solvent. The solvent is washed with water, dried and the solvent removed to provide the corresponding 1-[2,2-dimethoxy]ethyl-2-$R^1$,4-$R^2$,6-$R^3$ benzene (or corresponding dialkyl or diaralkyl analogs).

1-[2,2-Dimethoxy]ethyl-2-$R^1$,4-$R^2$,6-$R^3$ benzene (or corresponding dialkyl or diaralkyl analogs) is taken up in an organic acid suitably, but not limited to alkanoic acids for example acetic acid, preferably glacial acetic acid (utilized for its ready availability). A substantial excess, suitably between 3 and 6 equivalents, preferably 3–4 equivalents of a reducing metal are added. While other metals high in the electrochemical series may be employed, iron is preferred because of low cost and ease of handling. The mixture is brought to reflux, becomes exothermic, heating ceased until the exother subsides and then refluxed again for from 15 minutes to 1 hour. The mixture is cooled, poured into cold water, extracted with a suitable water immiscible polar organic solvent. The solvent is washed with water, dried and the solvent removed to provide the corresponding nitroindole.

EXPERIMENTAL

Example 1

β-N,N-Dimethylamino-2,4,6-trinitrostyrene:

A mixture of 2,4,6-trinitrotoluene (0.5 g, 2.2 mmol) and N,N-dimethylformamide dimethyl acetal (2.7 ml) was refluxed for 2 h under nitrogen atmosphere. A dark purple red product was separated. N,N-dimethylformamide dimethyl acetal was removed under reduced pressure to give the title compound (0.56 g, 90% yield). m.p.: 155–157° C.; IR (KBr): 1635, 1585, 1530 cm-1; $^1$H NMR (CDCl3): δ 3.05 (s, 6H, 2×CH3); 5.65 (d, J=13.17 Hz, 1H, α-CH); 6.87 (d, J=13.2 Hz, 1H, β-CH); 8.55 (s, 2H, Ar—H); UV: Imax: 474 nm (CH3CN).

In accordance with the above procedure but starting with 2-amino-4,6-dinitrotoluene, 2-chloro-4,6-dinitro-toluene and 4-chloro-2,6-dinitrotoluene in place 2,4,6-trinitrotoluene there are obtained β-N,N-Dimethylamino-2-amino-4,6-dinitrostyrene: $^1$H NMR (CDCl3): δ 3.15 (s, 6H, 2×CH3); 5.55 (d, J=13.1 Hz, 1H, α-CH); 7.50 (d, J=1.2 Hz, 1H, Ar—H); 8.20 (d, J=1.2 Hz,1H, Ar—H); 8.50 (d, J=13.2 Hz, 1H, β-CH); Mass (Cl): 253 (M+ +1); Imax: 492 nm (CH3CN), β-N,N-Dimethylamino-2-chloro-4,6-dinitrostyrene: m.p. 110–112° C.; $^1$H NMR (Acetone-d6)): δ 3.06 (s, 6H, 2×CH3); 5.28 (d, 1H, α-CH); 7.43 (d, 1H, β-CH); 8.26 (d, 1H, H-3); 8.37 (d, 1H, H-5); Mass: 271 (M+) and β-N,N-Dimethylamino-4-chloro-2,6-dinitrostyrene: m.p. 105–107° C.; $^1$H NMR (Acetone-d6)): δ 2.89 (s, 6H, 2×CH3); 5.16 (d, 1H, α-CH); 6.59 (d, 1H, β-CH); 8.0 (s, 2H, Ar—H); Mass: 271 (M+) respectively.

In accordance with the above procedure and starting with trinitrotoluene but utilizing 4-dimethylaminobenzaldehyde in place of dimethylformamide dimethylacetal the reaction yields β-[4-(N,N-diethylamino) phenyl]-2,4,6-trinitrostyrene.

Example 2

1-(2,2-Dimethoxy)ethyl-2,4,6-trinitrobenzene:

A solution of β-N,N-dimethylamino-2,4,6-trinitrostyrene (895 mg, 3.173 mmol), conc, hydrochloric acid (0.5 ml) in methanol (10 ml) was refluxed for 2–2.5 hr. The solvent was removed on rotavapor, residue was diluted with water and extracted with ethyl acetate. The organic layer was washed with water, brine solution and dried over anhydrous sodium sulfate. Removal of solvent gave the title compound (716 mg, 75%) which was purified by silica gel column chromatography using ethyl acetate/hexane. 1H NMR (Acetone d6): δ 3.276 (s, 6H, 2×OCH3); 3.611 (d, 2H, CH2); 4.636 (t, 1H, CH); 8.936 (s, 2H, Ar-H).

In accordance with the above procedure but starting with β-N,N-dimethylamino-2-chloro-4,6-dinitrostyrene and β-N,N-dimethylamino-4-chloro-2,6-dinitrostyrene in place of β-N,N-dimethylamino-2,4,6-trinitrostyrene there are obtained 1-(2,2-dimethoxy)ethyl-2-chloro-4,6-dinitrobenzene: $^1$H NMR (Acetone d6): δ 3.29 (s, 6H, 2×OCH3); 3.58 (d, 2H, CH2); 4.55 (t, 1H, CH); 8.59 (dd, 2H, Ar—H); Mass: (259 (M+—OCH3) and 1-(2,2-Dimethoxy)ethyl-4-chloro-2,6-dinitrobenzene: m.p. 84–850 C.; $^1$H NMR (Acetone d6): δ 3.25 (s, 6H, 2×OCH3); 3.42 (d, 2H, CH2); 4.54 (t, 1H, CH); 8.23 (s, 2H, Ar—H); Mass: (259 (M+—OCH3).

Example 3

4,6-Dinitroindole

A solution of 1-(2,2-dimethoxy)ethyl-2,4,6-trinitrobenzene (117 mg, 0.388 mmol) in glacial acetic acid (1 ml) was refluxed and iron powder (69 mg, 1.17 mmol) was added. The heating source was removed and the exothermic reaction was allowed to subside. Then refluxing was continued for 30 minutes. The reaction mixture was cooled, poured into cold water, extracted with ethyl acetate, washed with water, brine and dried over anhydrous sodium sulfate. Removal of solvent gave 4,6-dinitroindole as a yellow solid (56 mg, 70%). $^1$H NMR (Acetone d6): δ 7.28 (dd, H-2); 8.12 (d, 1H, H-3); 8.85 (m, 2H, H-5 & H-7). Mass: 208 (M+ +1).

In accordance with the above procedure but starting with 1-(2,2-dimethoxy)ethyl-2-chloro-4,6-dinitrobenzene and 1-(2,2-dimethoxy)ethyl-4-chloro-2,6-dinitrobenzene in place of 1-(2,2-Dimethoxy)ethyl-2,4,6-trinitrobenzene there are obtained 4-Chloro-6-nitroindole: $^1$H NMR (Acetone d6): δ 7.15 (m, 1H, H-2); 7.87 (t, 1H, H-3); 7.96 (d, 1H, H-5); 8.43 (m, 1H, H-7); Mass: 196 (M+) and 6-Chloro-4-nitroindole: $^1$H NMR (Acetone d6): δ 6.72 (m, 1H-H-2); 7.79 (t, 1H, H-3); 7.96 (d, 1H, H-5); 8.05 (d, 1H, H-7); Mass: 196 (M+).

Example 6

4,6-Dinitroindole 4,6-Dinitroindole was also prepared by refluxing β-N,N-dimethylamino-2-amino-4,6-dinitrostyrene (50 mg, 0.198 mmol) with catalytic amount of p-toluenesulfonic acid in methanol (5 ml) for 3.5 hr.

We claim:

1. 4-$Z^1$,6-$Z^2$ indole wherein $Z^1$ and $Z^2$ are the same or different and are halo or nitro has been provided at least one of said groups is nitro.

2. The compound of claim 1 where the halo group is chloro.

3. The compound of claim 1 wherein both $Z^1$ and $Z^2$ are nitro.

4. The compound of claim 1 wherein $Z^1$ is chloro and $Z^2$ is nitro.

5. The compound of claim 1 wherein $Z^1$ is nitro and $Z^2$ is chloro.

* * * * *